United States Patent [19]

Apgar et al.

[11] Patent Number: Plant 6,630

[45] Date of Patent: Feb. 28, 1989

[54] IVY PLANT

[76] Inventors: Paul Apgar; Lindi Apgar, both of 330 Estrelita Dr., Vista, Calif. 92084

[21] Appl. No.: 103,036

[22] Filed: Aug. 24, 1987

[51] Int. Cl.[4] ..... A01H 5/00

[52] U.S. Cl. ..... Plt./67

[58] Field of Search ..... Plt./67

*Primary Examiner*—Robert E. Bagwill

*Attorney, Agent, or Firm*—Calif Kip Tervo

[57] ABSTRACT

A new and distinct ivy named Susie Q of the species *Hedera helix,* which is particularly characterized by its extremely curly, undulated, and convoluted leaves.

5 Drawing Sheets

Our new discovery relates to improvements in ivy, and especially to a new, original, and distinct variety of ivy of the species *Hedera helix.*

The new plant is named "Susie Q" and is useful in the ways of other types of ivy; such as for climbing ground cover, ornamental potted plants, and the like.

We discovered the new plant in our nursery as a cultivated sport or off-shoot mutation of the ivy variety known as Holly Ivy. The plant has been asexually reproduced by us by cuttings in our nursery in Vista, Calif., into approximately 40,000 specimens. This new variety is outstandingly different from the parent, particularly in the appearance of the leaves. The leaves of the new plant are extraordinarily convoluted, curly and three-dimensional which gives the plant a rich, full, and luxurious appearance. Its distinct characteristics appear to be permanent and it has reproduced true to type for several years.

BRIEF DESCRIPTION OF THE DRAWINGS

FIG. 6 is a color photograph of the top of a mature leaf.

FIG. 7 is a color photograph of the bottom of the leaf of FIG. 6.

DETAILED DESCRIPTION OF THE VARIETY

Figure 4:
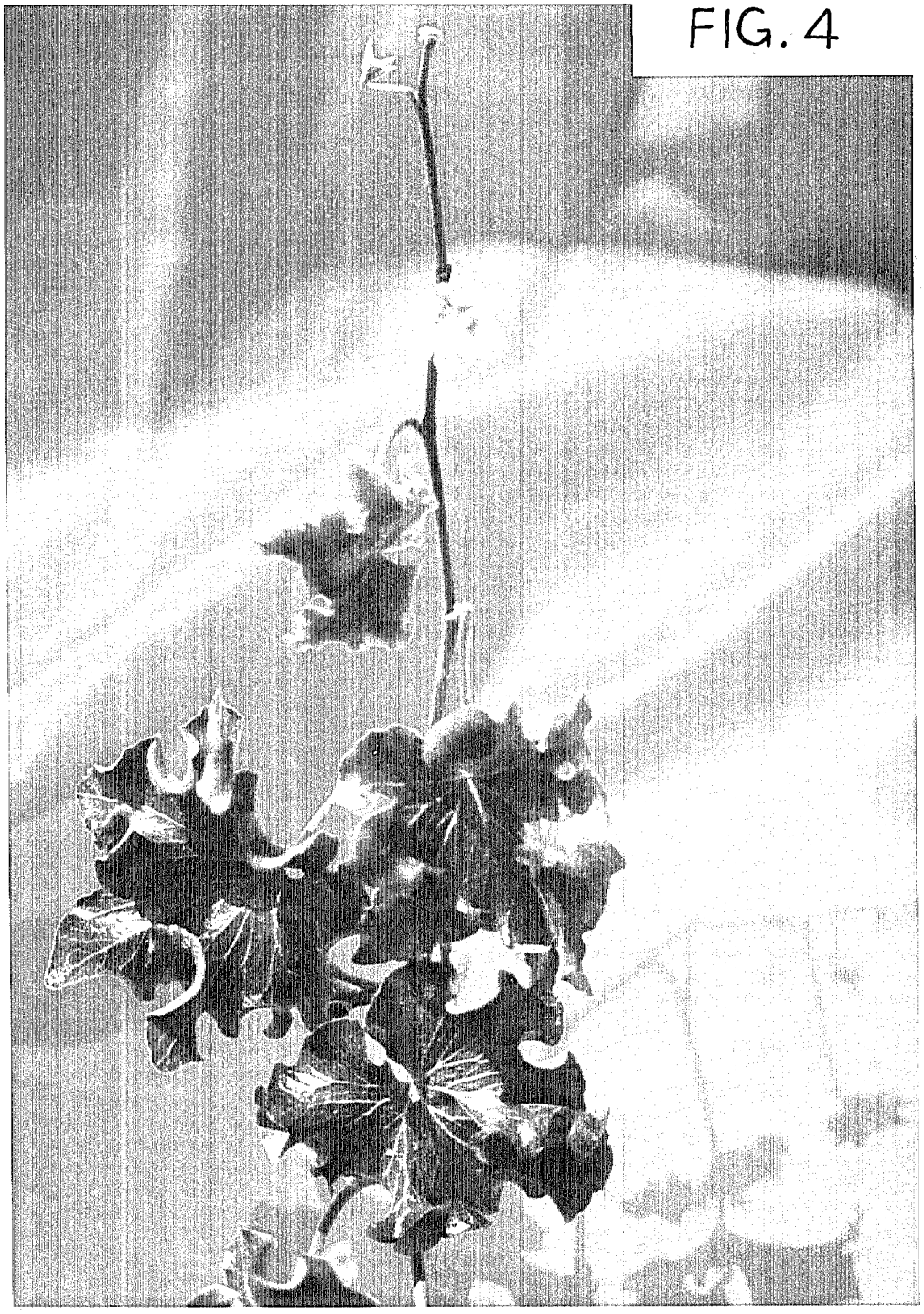
FIG. 4 is a color photograph showing the end portion of a vine, including mature and young leaves.

The color terminology is in accordance with Exotica Horticultural Color Guide, copyright 1962 Roehrs Company, Rutherford, N.J. as found in Exotica 3 (1970 edition) by A. B. Graf. Where no reference is given, the ordinary dictionary term is intended. The true color of the mature leaf is best show in FIG. 4. In the other photographs, the green is slightly lighter and duller than in real life.

Susie Q is a sport of an ivy commonly called Holly Ivy of the species *Hedera helix.* Susie Q is easily propagated from individual leaf cuttings. It has held its distinguishing characteristics thru succeeding propagations, and it has rooted in many types of soil. Its rooting is vigorous and rapid. It roots at, or very near, the joint of the vine and petiole, and roots in air. Susie Q is a good climber and grabber, and rapidly spreads out to cover the available growing area.

Figure 1:
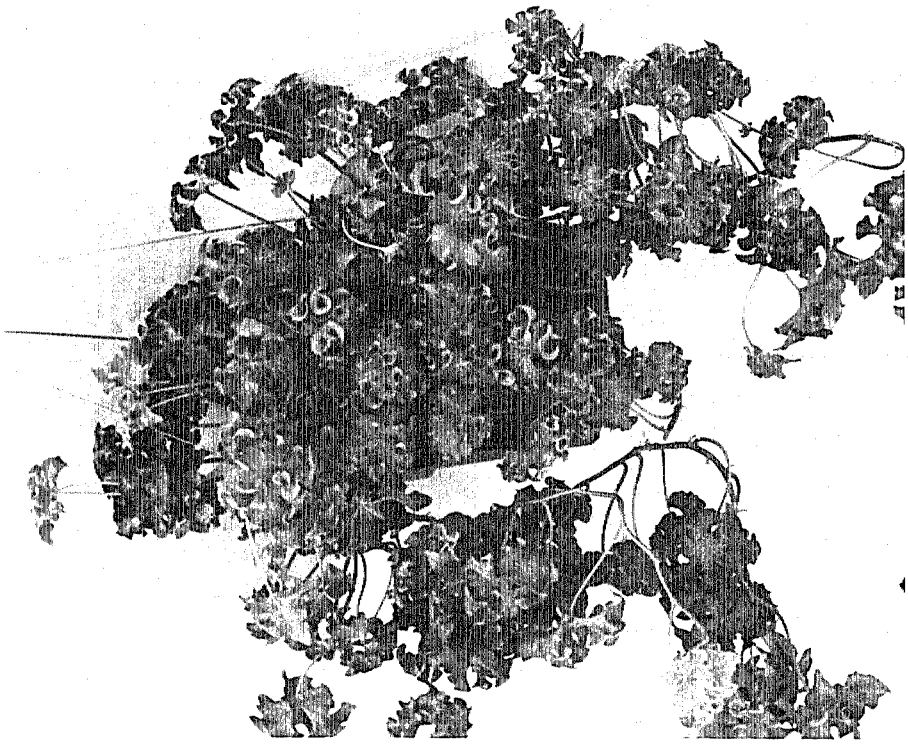
FIG. 1 is a color photograph presenting an overall view of the new variety, Susie Q, growing in a hanging pot.
Figure 2:
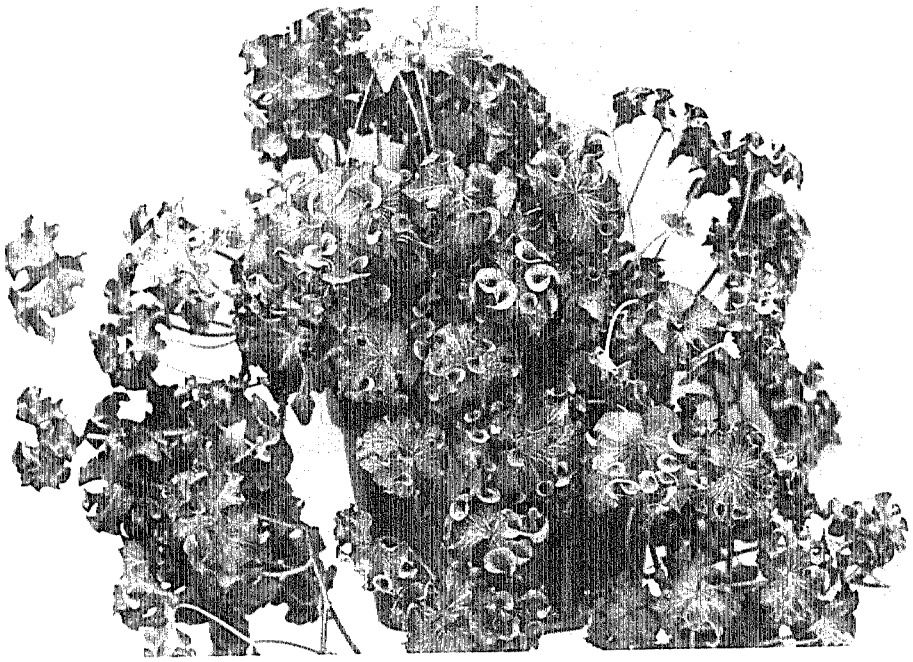
FIG. 2 is a close-up view of FIG. 1.
Figure 3:
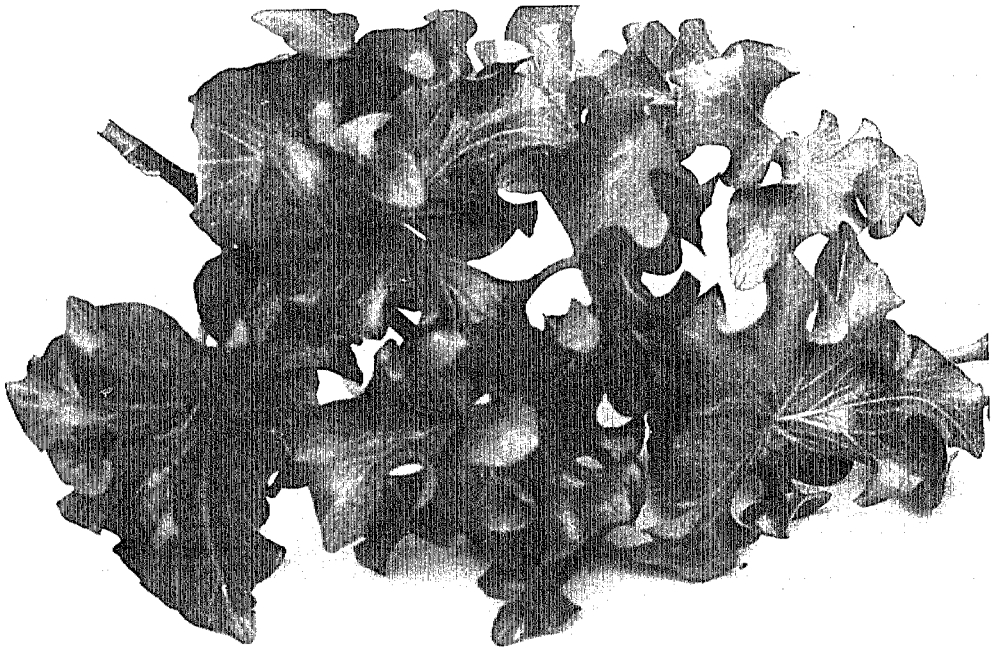
FIG. 3 is a color photograph showing the typical interrelationship and spacing of the leaves.

The vine is almost circular in cross-section. It is fairly smooth, shiny, and almost hairless. In color, the young vine is fern green 83 with a slight brown surface coloration. In the mature vine, the brown surface coloration is dominant and the underlying green has darkened to olive green 84. In a pot, the young vines grow upward for five to six inches and then bend over and begin to trail. As seen in FIG. 1, the vines are strong and robust. Whereas the vines of the parent plant trail in a more pendulous manner, the trailing vines of Susie Q are capable of reaching out and seeking to climb.

Internodes are one and one-fourth to one and one-half (1.25–1.5) inches in length. Succeeding internode sections are angled approximately twenty five to thirty (25–30) degrees from a straight line; the angle alternating from left to right with each successive node. Susie Q is self-branching at nodes.

The majority of petioles are approximately two (2) inches in length, although a few are three (3) inches or slightly longer. Petioles are circular in cross-section and are one-sixteenth (1/16) inch in diameter. They commence at nodes and are spaced alternately on opposite sides of the vine. The nodes closely resemble a "Y" with about a forty five to sixty (45–60) degree angle between the upper arms, whereby the next internode is disposed at a twenty five to thirty (25–30) degree angle from straight ahead in one direction and the petiole is disposed at approximately twenty to thirty (20–30) degree angle from straight ahead in the opposite direction. The petiole starts at this angle at the node and then quickly assumes an angle of approximately ninety (90) degrees to the vine. Very sparsely spaced thin woolly hairs cover the petiole. Near the node, the petiole is the color of the vine. It lightens and becomes greener as it approaches the leaf. The green of new petioles is citron 79, and that of mature petioles is lettuce green 81.

Figure 5:
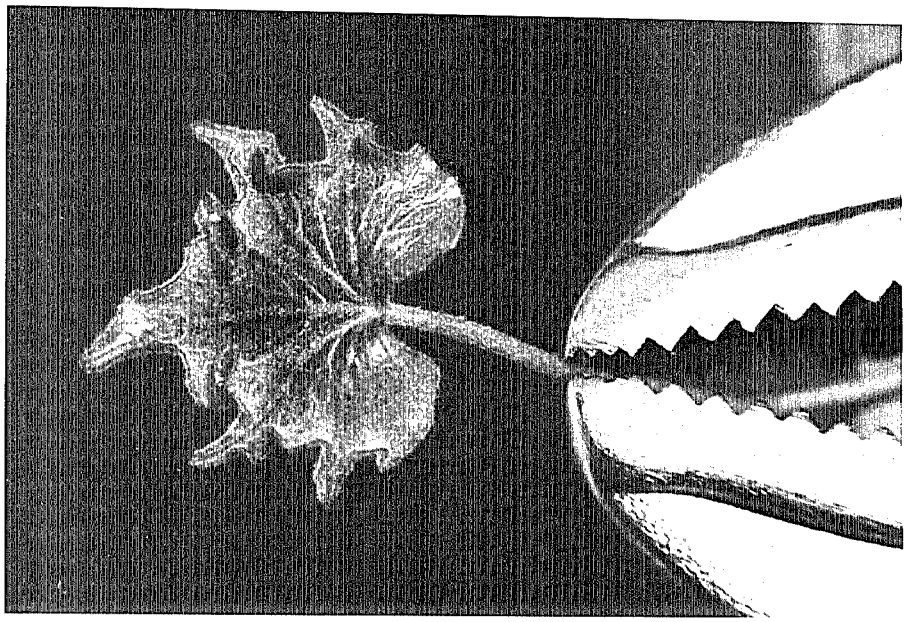
FIG. 5 is a color photograph of the top of a young leaf of Susie Q.

Leaves are palmately lobed. The general shape is cordate. FIG. 5, showing the top of a young leaf, also best shows the shape and structure of the leaf. This is so because these features are almost entirely obscured by the excessively curly and resulting three-dimensional nature of the mature leaf. The young leaf of Susie Q is similar to the mature leaf of the parent, except in color. The mature parent leaf is ivy green while the young Susie Q leaf is nile green 80 on both top and bottom.

The leaf has seven main lobes. The lobes are pointed. The large terminal lobe has an additional smaller lobe (mini-lobes) on each side. The sinus between the terminal and adjacent lateral lobe is deep while the sinuses between the other lobes are shallow. The young leaf is fairly flat and two-dimensional with a slightly undulated margin. The surface is shiny.

As the leaf matures the greens darken. A five week old leaf (not shown) has a top of meadow green 76 and a bottom of grass green 73.

A mature leaf is shown in FIGS. 6 and 7. The leaf assumes this shape and color by approximately twelve weeks. The top of the leaf is ivy green 70 and the bottom is meadow green 76. FIG. 6 is a top view and FIG. 7 is a bottom view of a mature leaf. The margin of the mature leaf becomes extremely undulated and the leaf becomes convoluted and assumes a three-dimensional appearance. The sinus between the terminal lobe and adjacent lateral lobes may include five to ten major curls and many small edge wiggles. The basal lobes may so touch or overlap one another that the leaf almost appears to be peltate.

The leaves are strong and tough. They are very pliable and can be bent or crushed without ripping or tearing. The surface is slightly waxy. The shiny surface of the young leaf becomes quite dull as the leaf matures and the number of small surface hairs increases.

Leaf veins are of the branching type and originate at the petiole. There are some interconnection between veins. Both top and bottom vein surfaces are chartreuse 78. The veins are very visible on the top surface both because they are slightly raised and because of their color. Veins on the bottom surface are also easily seen even though they are almost flush with the surface because of their color and shininess.

Figure 8:
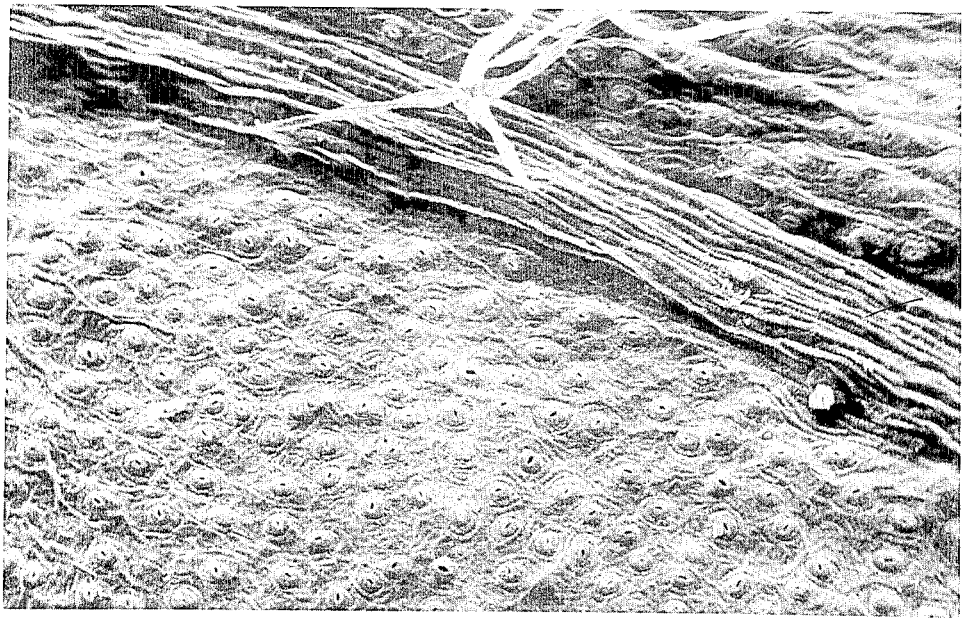
FIG. 8 is a black and white electron microscope photograph at eighty two power (82×) of the top surface of a mature leaf of the new variety.
Figure 9:
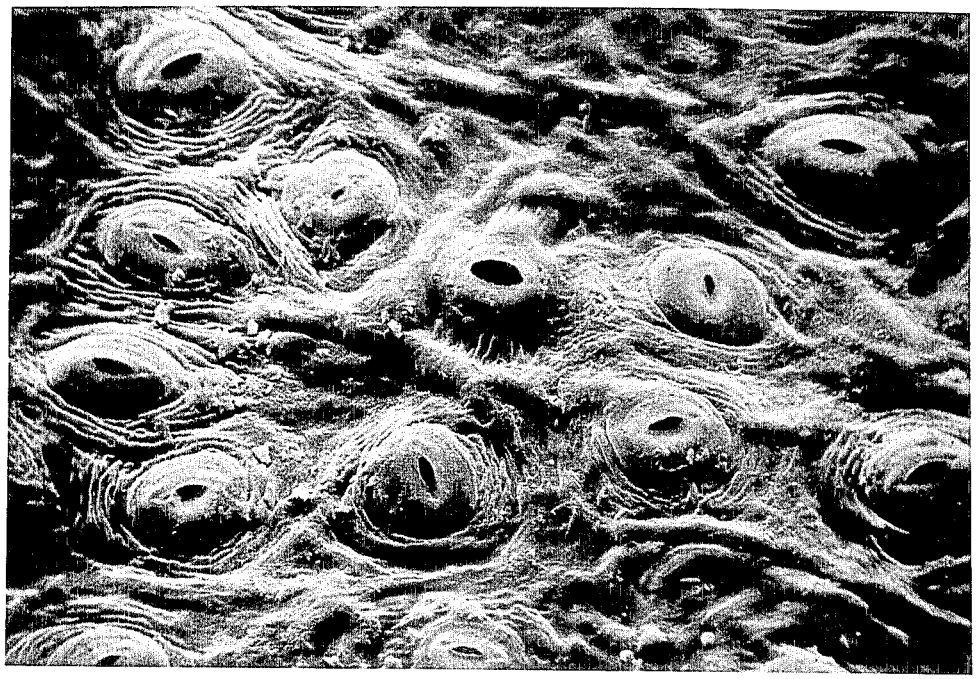
FIG. 9 is a black and white electron microscope photograph at four hundred and twenty power (420×) of the top surface of a portion of a mature leaf of Susie Q.

In FIGS. 8 and 9, mature leaves were freeze dried, silver coated, and photographed in black and white with an electron microscope. FIG. 8 is an eighty two power (82×) photograph of the top surface of a mature leaf of the new variety. A vein, hairs, and stomata are visible.

FIG. 9 is a four hundred and twenty power (420×) photograph of the top surface of a portion of a mature leaf of Susie Q. The shape of the stomata are more clearly seen.

We claim:

1. A new and distinct variety of ivy substantially as herein described and illustrated.

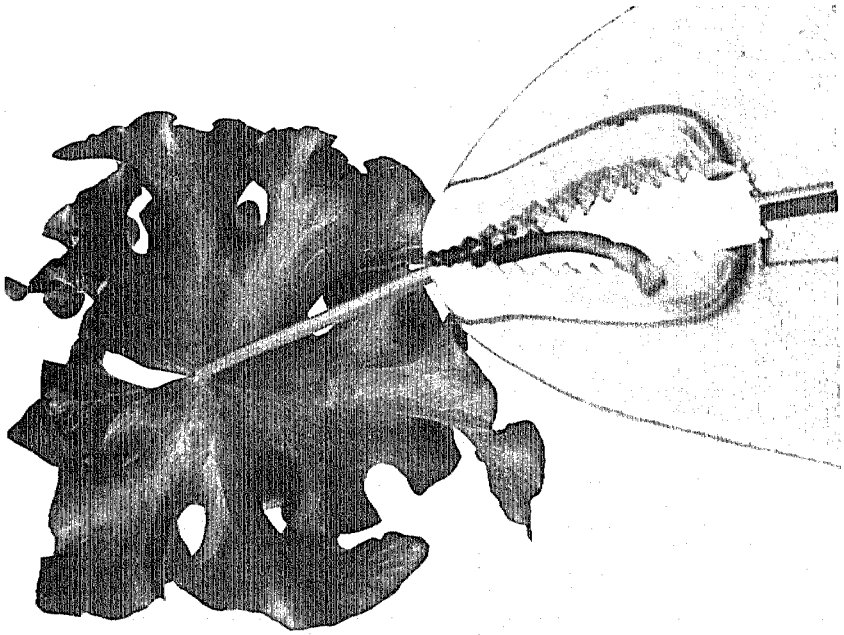
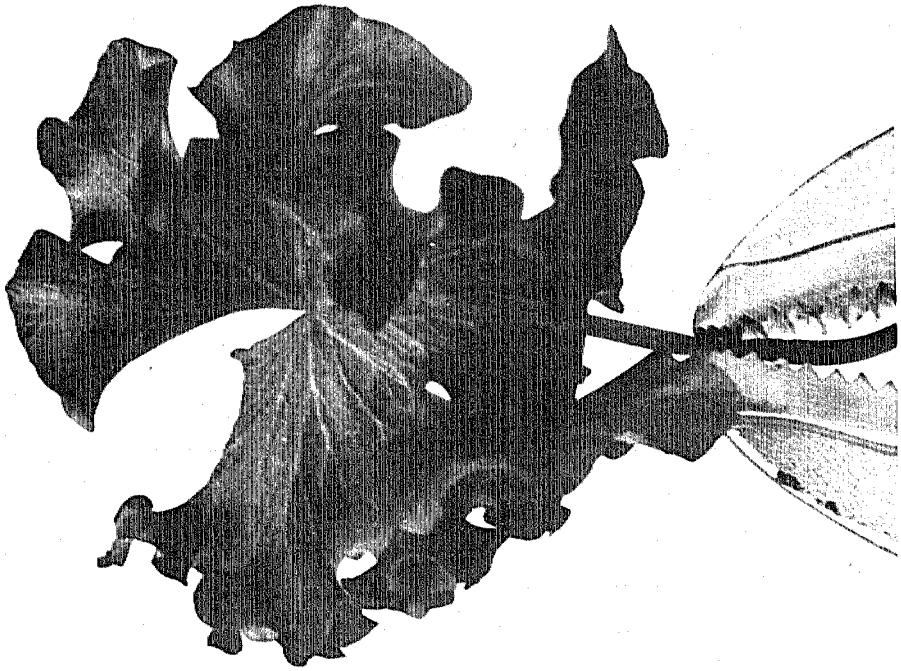

* * * * *